United States Patent
Cattide et al.

(10) Patent No.: US 10,772,978 B2
(45) Date of Patent: Sep. 15, 2020

(54) STERILIZATION SYSTEM HAVING AN IMPROVED THERMODYNAMIC CYCLE AND RELATED METHOD

(71) Applicant: W & H STERILIZATION S.r.l., Brusaporto (Bergamo) (IT)

(72) Inventors: Antonello Cattide, Brusaporto (IT); Marino Luigi Magno, Brusaporto (IT); Klaus Maier, Brusaporto (IT)

(73) Assignee: W & H STERILIZATION S.R.L., Brusaporto (Bergamo) (IT)

( * ) Notice: Subject to any disclaimer, the term of this patent is extended or adjusted under 35 U.S.C. 154(b) by 286 days.

(21) Appl. No.: 15/855,582

(22) Filed: Dec. 27, 2017

(65) Prior Publication Data
US 2018/0177903 A1   Jun. 28, 2018

(30) Foreign Application Priority Data
Dec. 27, 2016   (IT) .......................... 102016000131201

(51) Int. Cl.
*A61L 2/07*   (2006.01)
*A61L 2/26*   (2006.01)

(52) U.S. Cl.
CPC ........ *A61L 2/07* (2013.01); *A61L 2/26* (2013.01); *A61L 2202/14* (2013.01); *A61L 2202/24* (2013.01)

(58) Field of Classification Search
CPC ...................................... A61L 2/07; A61L 2/26
USPC .......................................................... 422/3
See application file for complete search history.

(56) References Cited

U.S. PATENT DOCUMENTS 6,379,613 B1 *   4/2002   Stempf ...................... A61L 2/24
                                                        122/235.29
7,641,852 B1     1/2010   McPhail et al.

FOREIGN PATENT DOCUMENTS

| DE | 10 2012 010739 A1 | 5/2013 |
| EP | 0 852 146 A2 | 7/1998 |
| EP | 0 922 247 A1 | 4/2000 |
| EP | 1 175 231 A1 | 1/2002 |
| GB | 993883 A | 6/1965 |
| GB | 1 137 409 A | 12/1968 |
| WO | 00/59553 A1 | 10/2000 |

OTHER PUBLICATIONS

IT Search Report, dated Sep. 12, 2017, from corresponding IT application No. 102016000131201.

* cited by examiner

*Primary Examiner* — Kevin Joyner
(74) *Attorney, Agent, or Firm* — Nixon & Vanderhye

(57) ABSTRACT

A sterilization method and system are disclosed, where a sterilization cycle includes at least an evacuation step of a sterilization chamber is performed one or more times and provides that: the chamber is isolated from the condenser; at least a steam generator is operated to inject a predetermined amount of heated steam directly into the condenser; the steam in the condenser is cooled and condensed, so as to reduce its volume and accordingly lower the pressure within the condenser to below that present in the sterilization chamber; and the condenser is placed in communication with the sterilization chamber to perform an evacuation.

12 Claims, 7 Drawing Sheets

STERILIZATION SYSTEM HAVING AN IMPROVED THERMODYNAMIC CYCLE AND RELATED METHOD

FIELD OF THE INVENTION

The present invention relates to a sterilization system for various applications, e.g. autoclaves, thermodisinfectors, pasteurisers, dryers and so on. In particular, the invention relates to such a system with an improved thermodynamic cycle and the related operating method.

BACKGROUND

Although the principles offered here may relate to any sterilization system where high-temperature steam is used, for sake of convenience we will refer almost exclusively to an ambulatory autoclave (e.g., for use in dental and veterinary clinics, for tattoo artists and beauticians), but it is to be understood that this does not limit the scope of the application of the invention.

In medical clinics, particularly in dental clinics, it has long been known that small size autoclaves are used to sterilize small manual tools or dental handpieces. The autoclaves usually have a sterilization chamber, which is for the most part empty and provided with appropriate equipment (such as baskets, trays or storage compartments) to house the devices to be sterilized (i.e. the workload). The chamber is provided with an opening to introduce the load and can be tightly closed (sealed) to carry out the desired sterilization cycle.

The sterilization process takes place according to typical cycles, often compliant with a standard, with the aid of equipment and operation devices for the sterilization chamber. Typically, even if this should not be considered as a limitation, the following devices are provided:
- a pair of water tanks, one for clean water, which is picked up to produce the steam and one for waste (used) water, deriving from the condensation of the steam;
- a pump to move the water;
- a steam generator, in which clean water is injected to produce the steam that acts as a working fluid;
- a condenser, to carry out the steam condensation and its related discharge towards the collection waste tank;
- a vacuum pump, intended to empty the sterilization chamber;
- and a series of electrovalves and ducts to put the equipments and devices in communication each other in the desired modes and times.

An exemplary autoclave of this type is known from EP 992.247, whose circuit scheme is shown in FIG. 1 as an example of prior art.

A sterilization process normally involves—after the autoclave loading and its sealing—an emptying cycle of the sterilization chamber air, a pressurization cycle of the chamber with high temperature (about 120°-145° C.) and pressure (up to about 2-3 bar) steam and finally an emptying cycle of the chamber and subsequent drying. In the pressurization cycle, the actual sterilization of the tools takes place inside the chamber, while the final phase of emptying and drying is used to ensure a perfect drying of the tools for their proper preservation.

This general operation process is an example of what actually takes place, because there are many operation variations to achieve a greater efficiency of the process and optimal energy yields.

One of the most critical and expensive components in an autoclave is the vacuum pump, which is used to achieve the emptying of the sterilization chamber. This device, besides involving a cost, often causes problems, both because it has moving elements—therefore subject to wear and/or fatigue—and because it treats a fluid (steam) that can undergo changes in status (from gaseous to liquid) with inevitable associated problems (due to the biphasic flow).

In the past, it has already been proposed to produce vacuum in the sterilization system using fluids, rather than a vacuum pump. For example GB 1137409 describes a sterilization system where a complex hydraulic circuit is used with related water tanks, in order to obtain a pressure reduction. However, the system is complex and difficult to implement and control.

GB 993.883 discloses another autoclave system where a generator is connected both to the sterilization chamber and to a condenser immersed in a water tank. This configuration is intended to regulate the water level in the generator to prevent the heating elements from being exposed, but does not provide any fluid-dynamic interaction between the generator and the condenser. DE102012010739 shows another autoclave system, wherein a condenser is partly in communication with a steam generator, but the evacuation of the sterilization chamber is still determined by vacuum pumps. WO00/59553 and EP852146 illustrate other autoclave configurations with sterilization cycles which still only use vacuum pumps to evacuate the sterilization chamber. EP 992.247 owned by the same applicant, describes a further autoclave circuit wherein a separated small cold lung of the system is used to cooperate in the emptying of the sterilization chamber.

The applicant has the aim of providing a sterilization system and a related operation process, which could achieve a good operation of the sterilization cycle and in particular the emptying of the sterilization chamber, eliminating or reducing the contribution of a vacuum pump and modifying to the minimum necessary the existing circuits for traditional autoclaves provided with vacuum pump.

SUMMARY OF THE INVENTION

The object of the present invention is therefore to overcome the aforementioned drawbacks by providing a steam sterilization system and an operation process which can complete a sterilization cycle without need for a mechanical vacuum pump.

Such object is achieved by means of an equipment and a method as described in their essential features in the appended main claims.

Other inventive aspects of the invention are described in the dependent claims.

BRIEF DESCRIPTION OF THE DRAWINGS

Further characteristics and advantages of the equipment and method according to the invention will be more apparent from the following detailed description of a preferred embodiment, given by way of example and illustrated on the accompanying drawings, wherein.

DETAILED DESCRIPTION OF PREFERRED EMBODIMENTS

Figure 1:
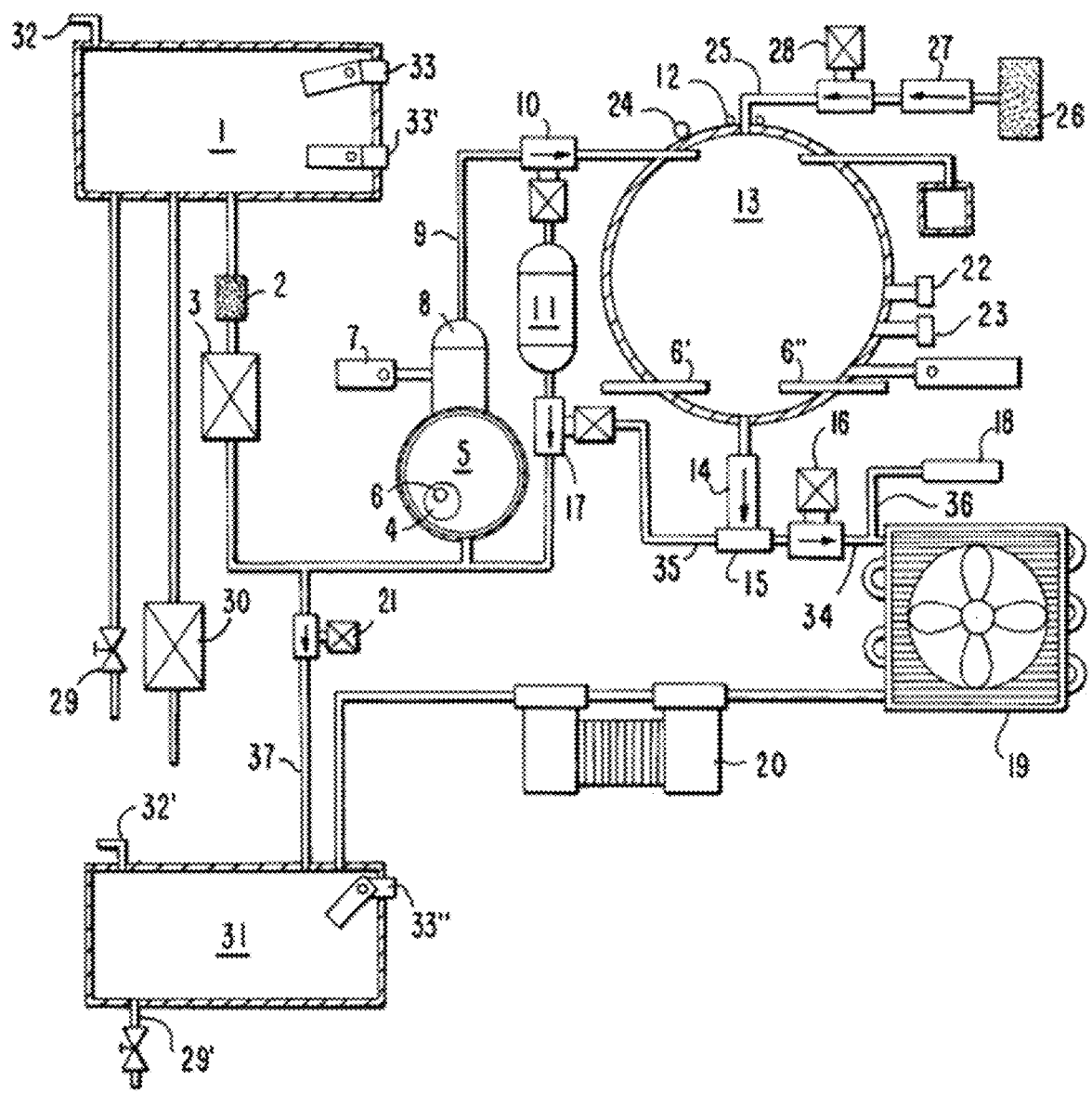
FIG. 1 is a schematic view of a hydraulic circuit in an autoclave of prior art.
Figure 2:
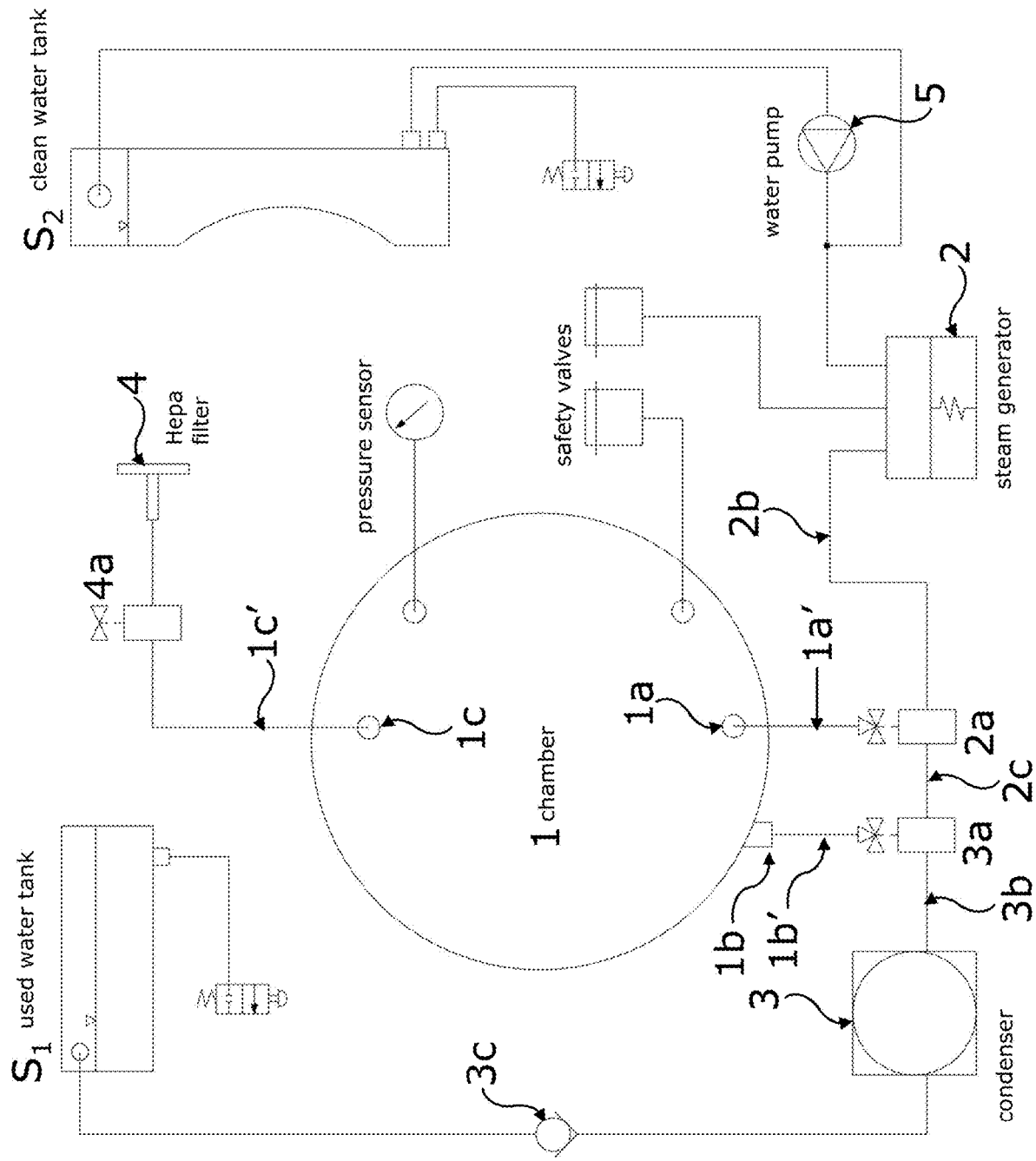
FIG. 2 is a schematic view of an exemplary hydraulic circuit in a sterilization autoclave according to the invention.

The scheme of FIG. 2 shows the main component of an autoclave, which is taken as an exemplary scheme of a steam sterilization system.

A sterilization chamber 1 is in the form of a sealingly closable container, able to withstand the sterilization pressure, generally cylindrical in shape. Chamber 1 is generally heated by various systems.

Fittings are provided on the wall of the container 1 to connect the interior of the chamber 1 to a series of operating devices. In particular, the container 1 is provided, at least, with an inlet connector 1a and with discharge means 1b. The inlet connector 1a is intended to be connected to a steam generator 2, through the related pipe 1a' and a controlled inlet valve 2a, from which it receives sterilization steam. The discharge means 1b are intended to be connected to a condenser 3, through the related pipe 1b' and controlled discharge valve 3a, in which the steam coming out from the sterilization chamber is typically condensed.

In the embodiment described in FIG. 2, the inlet 2a and discharge valves 3a are in the form of two separate three-way electrovalves. In this case, a loading inlet 2b connects the generator 2 to a first port $2a_1$ of the inlet valve 2a, then a junction pipe 2c is provided which connects a second port $2a_2$ of the valve 2a to a second port $3a_2$ of the valve 3a and, finally, a discharge pipe 3b is provided which connects a first port $3a_1$ of the valve 3a to the condenser 3. The two valves 2a and 3a are then connected respectively to the pipes 1a' and 1b' through the respective third ports $2a_3$ and $3a_3$.

However, it is not excluded that the flow control between chamber 1, generator 2 and condenser 3 can be managed differently; for example, the inlet 2a and discharge valve 3a could be integrated into a single, more complex, controlled valve.

What is relevant for the purposes of the invention is the provision of a valve system which allows to alternately connect and isolate the sterilization chamber 1 and the condenser 3 with the generator 2.

On the wall of the chamber 1 a vent connector 1c is also provided for the connection to an air intake 4, provided with a suitable filter, suitable to allow ambient air to flow into the chamber, to rebalance the pressure before opening the autoclave. Along a connection pipe 1c' between the vent connector 1c and the air intake 4, a controlled vent valve 4a is provided.

Finally, the sterilization chamber 1 can have connectors to a pressure sensor, a safety overpressure valve, a temperature sensor and more.

The condenser 3 is also connected to a first tank $S_1$ of the waste used water through a discharge valve 3c, preferably a check valve or a non-return valve with automatic operation. In other words, the discharge valve 3c places the condenser 3 in communication with the ambient pressure and, when it is closed, it isolates the condenser from the external environment. A second tank $S_2$ of clean water is connected to a water pump 5. The latter is controlled so as to inject water into the steam generator 2 as required.

According to the invention it is possible to reach emptying levels of the sterilization chamber 1 equal to or higher than those obtainable by using mechanical vacuum production systems, such as, for example, vacuum pumps.

With an original arrangement of the related connections between chamber 1, steam generator 2 and condenser 3, and by using a suitable operating mode of the valves, it becomes possible to exploit the steam condensation in the condenser 3 to produce a thermodynamic effect of evacuation of the sterilization chamber.

In fact, according to the invention, an arrangement is provided in which the steam generator 2 can be connected directly (i.e. without any other equipment having a thermodynamic effect on steam) to the condenser 3 to introduce steam. The condenser is isolated from the external environment by means of the discharge valve 3c, so that the cooling of the steam inside it results in a reduction in pressure of the circuit including the condenser which can be used to empty the sterilization chamber 1 when the latter is placed in communication with the condenser 3. The pressure reduction in the condenser 3, when the discharge valve 3c is closed, can preferably be achieved (but it is not the only possible mode) by completely separating/isolating the condenser 3 also from the sterilization chamber 1 and from the generator 2, by means of appropriate valves.

The steam condensation causes a pressure and volume reduction thereof in the condenser 3 and chamber 1 system, suitably isolated from the electrovalves 2a and 3a. The continuous change in state of the vapour, from gaseous to liquid, in the condenser causes a flow between chamber 1 and condenser 3 which stops when the system has reached the pressure equilibrium. According to the invention, this flow is cyclically restarted, allowing to reach ever lower pressure levels (which correspond to higher emptying levels of the sterilization chamber 1).

It is therefore relevant for the purposes of the invention, that the connections and the valves are arranged to be able to isolate chamber 1, generator 2 and condenser between them in specific phases of the process and therefore establish low pressure cycles in the condenser 3 which allow to evacuate the sterilization chamber 1 without resorting to a mechanical pump.

Figure 3:
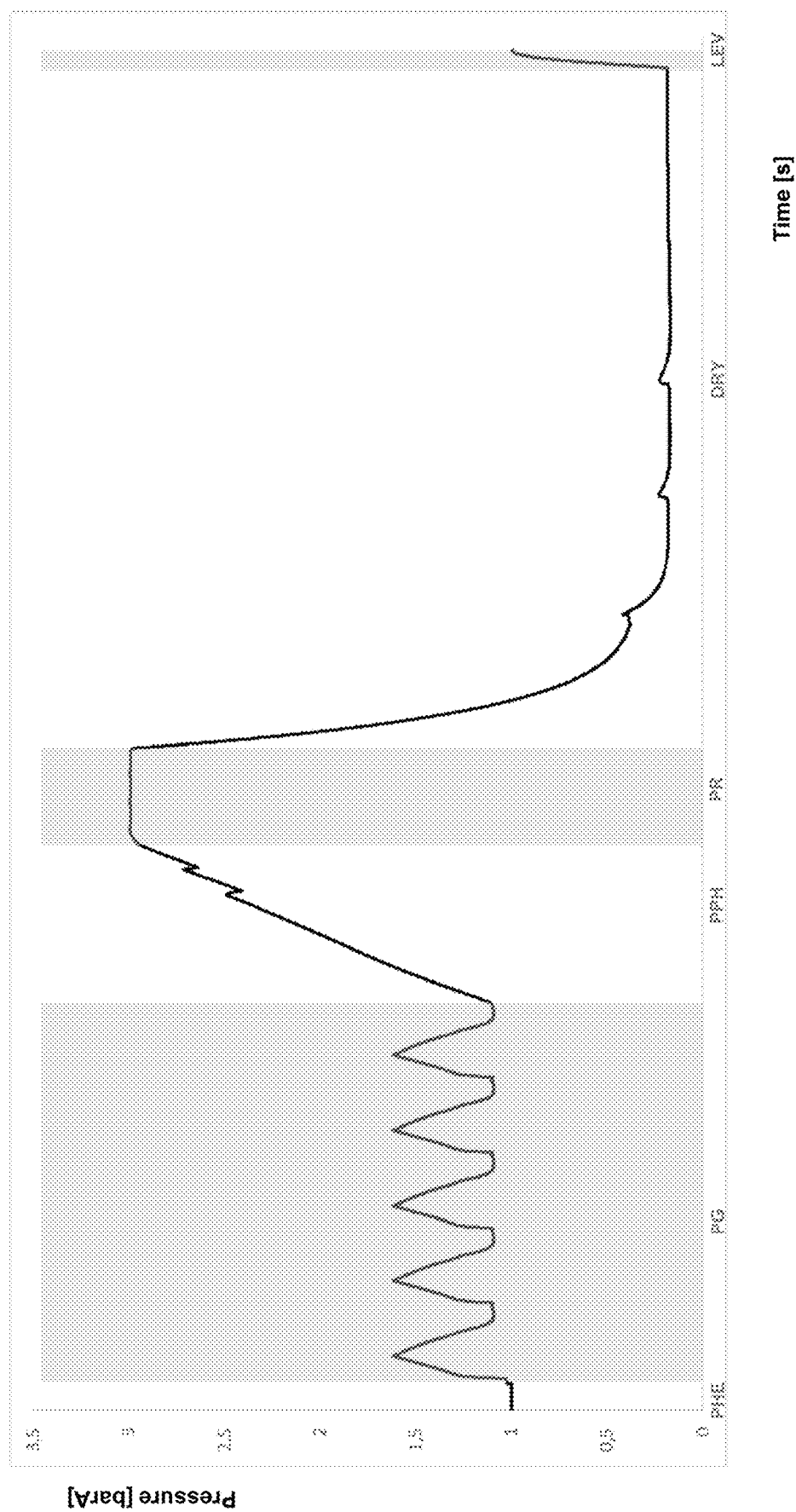
FIG. 3 is a graph of the pressure in the sterilization chamber as a function of the time during the process according to an embodiment of the invention.
Figure 4:
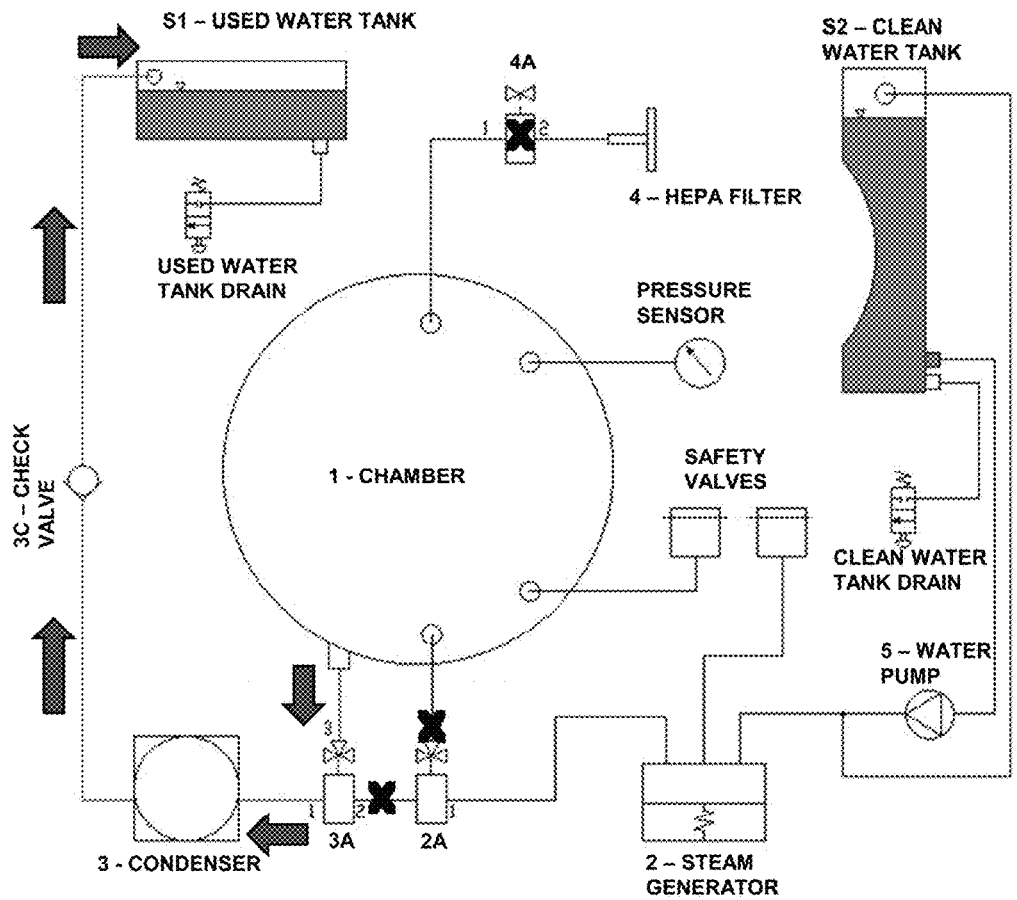
FIG. 4A represents the same graph of FIG. 3, in which a specific part of a drying cycle is highlighted.
FIG. 4B is a schematic view similar to that of FIG. 2, in an operational state corresponding to the cycle portion highlighted in the respective FIG. 4A.
Figure 4A:
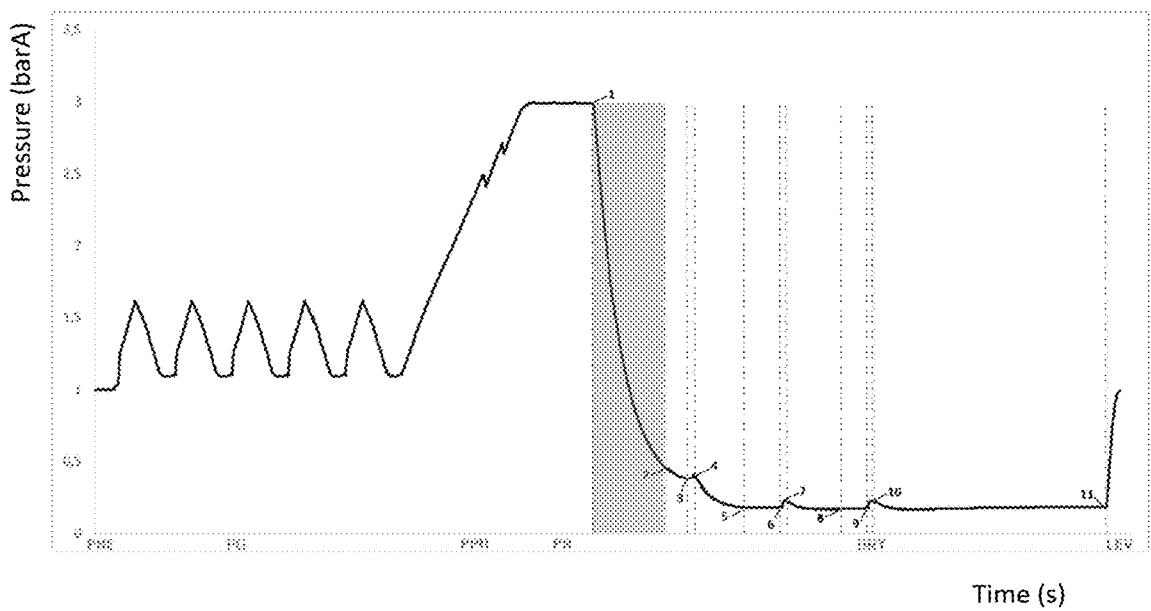
Figure 5:
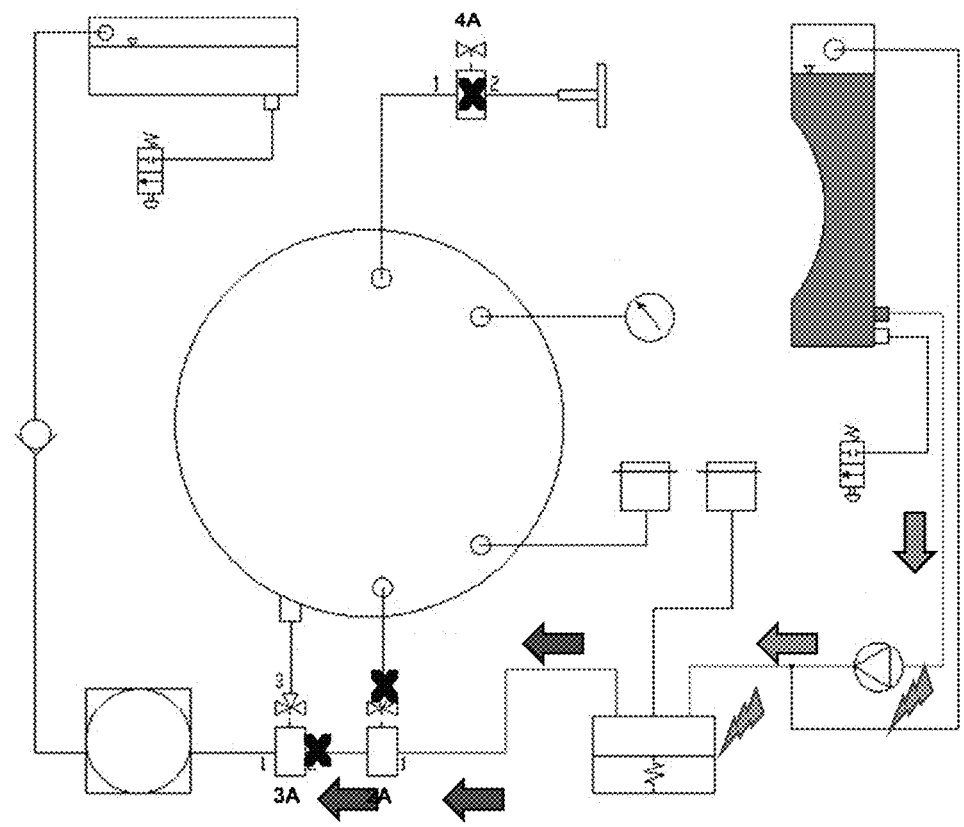
FIGS. 5A-7B are views similar to the homologous ones of FIGS. 4A and 4B, of successive phases of steam injection and emptying of the sterilization chamber.
Figure 5A:
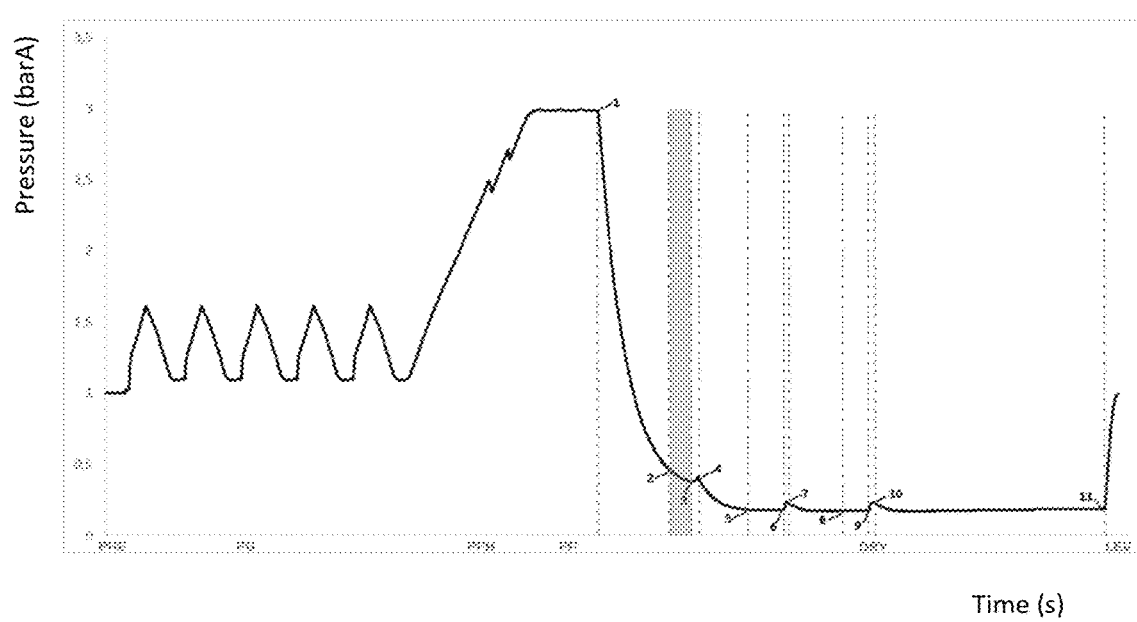

To better understand this operating mode, reference is now made to the embodiment illustrated in FIG. 3 and following.

FIG. 3 shows a graph representing the pressure with respect to time within the sterilization chamber 1, during an exemplary process of the invention. As a non-limiting example, a preliminary phase is provided with a preheating step PHE and an air evacuation step PG obtained with pressure pulses in the sterilization chamber 1. Then there is an actual sterilization cycle, with a first step PPH of temperature (for example up to 145° C.) and pressure (for example up to 3 bar) increase and then the maintenance of a plateau condition PR for the time necessary to complete the sterilization.

Then the actual emptying and drying DRY cycle takes place, in which the original sequence of the invention is effectively applied. The latter is analyzed in greater detail in some of its phases in FIGS. 4A-7B.

In the first phase of the emptying and drying cycle (FIG. 4A) the greatest pressure drop occurs. The chamber 1 is isolated from the generator 2 (valve 2a placed in position 1-2, i.e. communication between the ports $2a_1$ and $2a_2$) and it is put into communication with the condenser 3 (valve 3a placed in position 1-3), connected in turn to the discharge towards the first waste water tank $S_1$ (see FIG. 4B). The residual high pressure (e.g. 3 barA) in chamber 1, tends to quickly balance with the ambient pressure existing in the condenser 3.

In the meantime, keeping the steam generator isolated from the sterilization chamber 1—to prevent other steam from ending up in chamber 1 (which is drying)—it is possible to generate a small water injection into the steam generator, to produce and increase the steam pressure inside it (FIG. 5B) in preparation for the next operation step.

Figure 6:
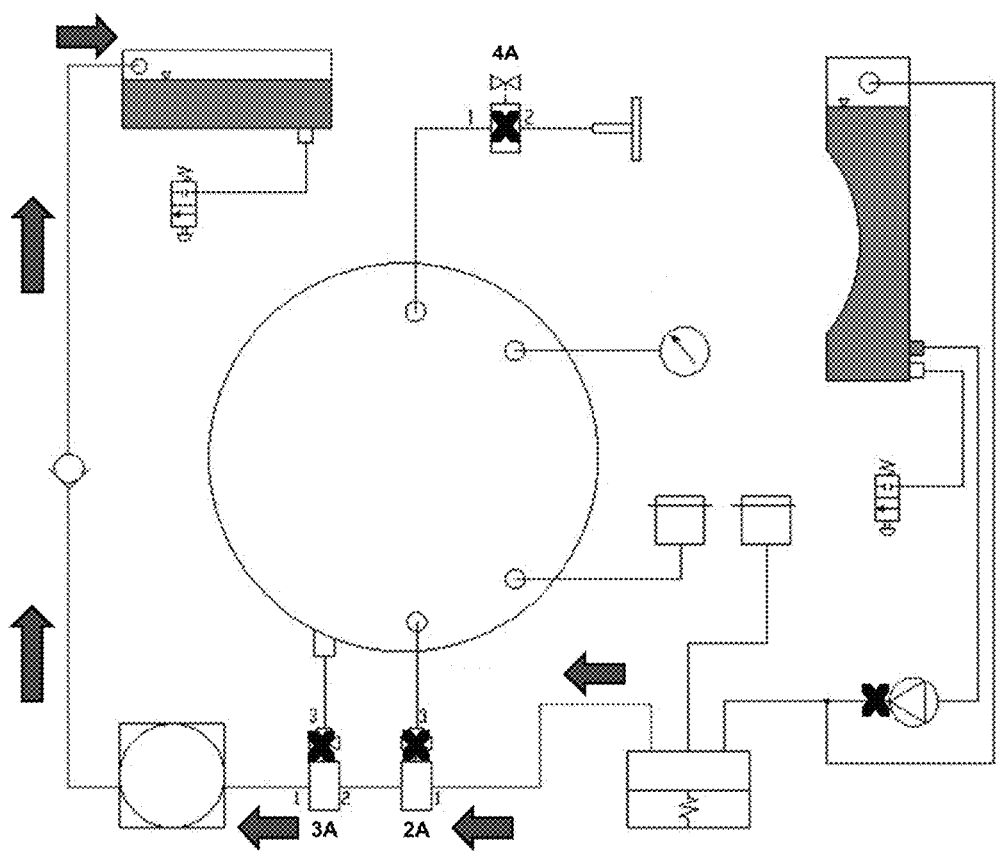
Figure 6A:
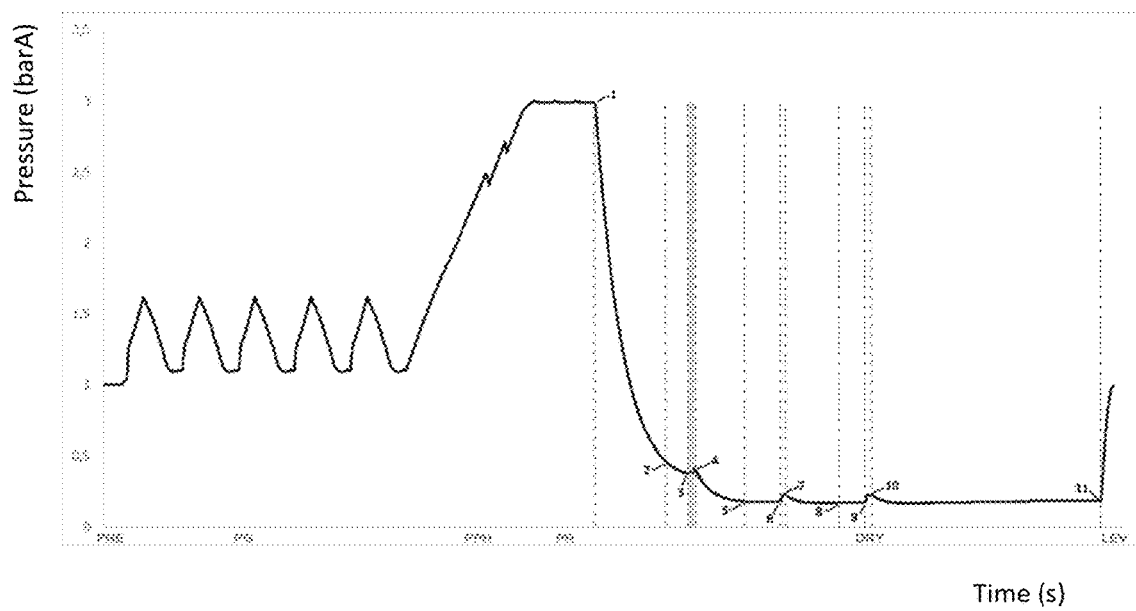

Subsequently (FIG. 6B) the chamber 1 is completely isolated—which thus stabilizes inside pressure (FIG. 6A)—and the steam generator 2 is put in communication with the condenser (valve 3a placed in position 1-2). The steam generated in the generator 2 enters the condenser 3 and partially exits through the valve 3c, pushing out condensate from the condenser.

Figure 7:
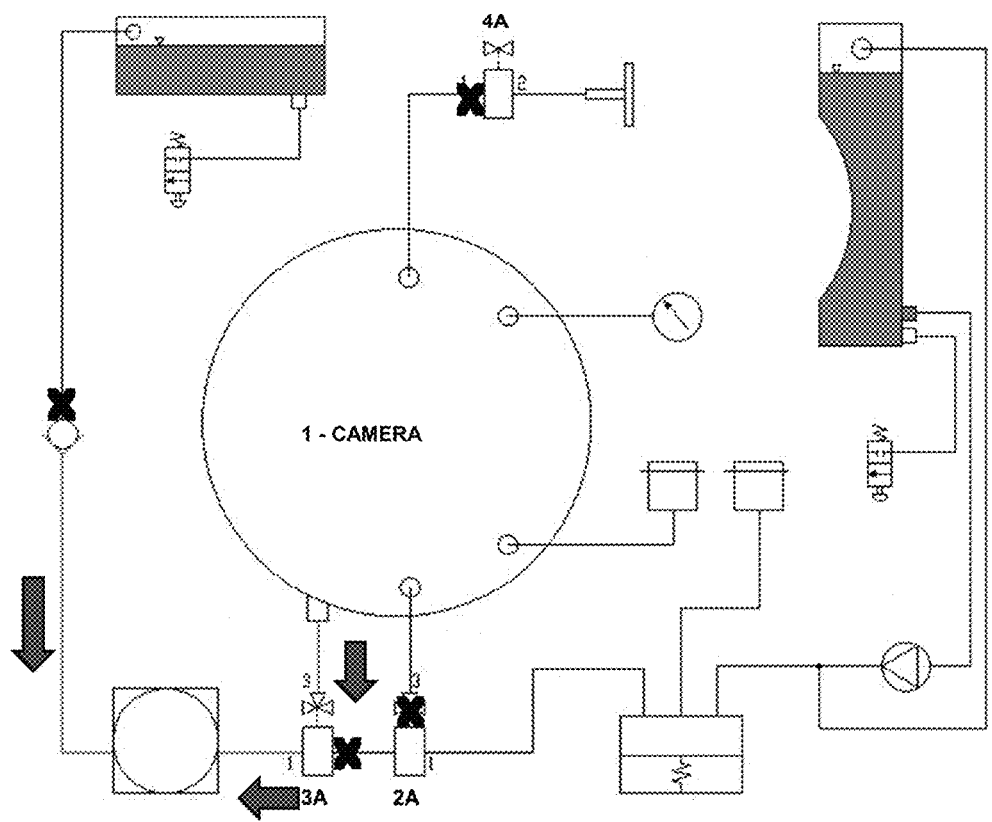
Figure 7A:
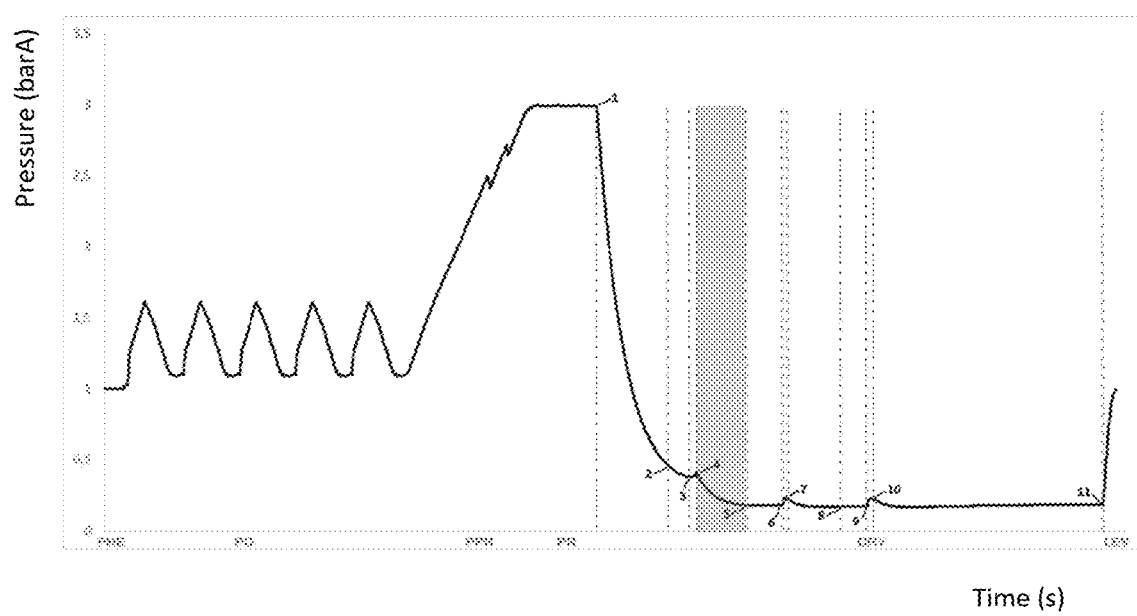

Then (FIG. 7B) the valve 3a is switched so as to put the sterilization chamber 1 in communication with the condenser 3, possibly also isolating the generator 2 through the valve 2a. As the condenser begins to cool the steam, there is a reduction in volume and therefore in pressure (FIG. 7A); the valve 3c is closed (or closes automatically if it is in the form of a check valve) and while the steam cools and condenses, the circuit including the condenser begins to go at low pressure. The pressure inside the condenser 3 stabilizes at a value lower than the ambient atmospheric pressure and the existing one in the sterilization chamber 1, thus producing a progressive emptying of the latter.

Subsequently the same process can be repeated until the desired emptying of the sterilization chamber has been achieved.

In brief, the method of the invention provides for injecting steam directly from the generator 2 to the condenser 3—i.e. a device designed for cooling and condensing the steam up to the liquid state—in which, due to the cooling of the steam in the gaseous state, it is possible to determine a reduction in the volume of the fluid and therefore a lowering of pressure: once it is placed in communication with the sterilization chamber, it acts as a point of low pressure for the emptying and drying of the sterilization chamber.

The steam injection into the condenser can be carried out at different stages of the sterilization cycle, preferably in a phase in which the sterilization chamber 1 is isolated both from the generator 2 and from the condenser 3.

As can be understood from the above description, through the configuration and the operation method of the invention, it is possible to fully achieve the purposes stated in the introduction.

In fact, even without the presence of a vacuum pump, by performing a series of thermodynamic cycles of steam condensation—putting the generator 2 in communication with the condenser 3 when the chamber 1 is isolated—it is possible to obtain an effective emptying and drying inside the sterilization chamber. This allows to greatly reduce the economic and technological problems related to the operation of a mechanical pump.

It is however understood that the invention is not limited to the particular configuration illustrated above, which represents only a non-limiting example of its scope, but that numerous variants are possible, all within the reach of a skilled in the art, without thereby departing from the scope of the invention itself.

For example, in the embodiment described in detail above, it is not foreseen to carry out an initial cycle of suction emptying of the sterilization chamber. Nothing prevents, however, to apply the principles taught with the invention, to obtain a thermodynamic emptying cycle even in any phase before the sterilization phase, for example immediately after closing the autoclave to eliminate the air inside the chamber (air that has insulating properties and makes the action of steam on the devices to be sterilized less effective—especially if they are porous or with internal cavities).

Furthermore, although the two inlet 2a and discharge valves 3a have been illustrated connected to each other—then with a circuit which provides for a passage of steam from the generator 2 to the condenser 3 through both valves—a similar principle operation can also be obtained with the inlet valve 2a connected directly to the chamber 1 and to the condenser 3, without connection between the two valves 2a and 3a. It is also possible to provide two separate single-way valves between the steam generator and the chamber 1 and the condenser 3: therefore it is more appropriate to indicate that an injection valve must be provided between the generator and the condenser which, in the illustrated embodiment, coincides with the inlet valve which also acts against the sterilization chamber.

In other words, the teaching of the invention can also be exploited in systems in which, for example:

the hydraulic circuit has a connection between the steam generator and the condenser, without this connection passing through the sterilization chamber;

the hydraulic circuit provides that the water injection carried out in the steam generator takes place with direct and/or indirect communication towards the condenser;

the hydraulic circuit has one or more connections between one or more steam generators and one or more condensers, without these connections having to pass through the sterilization chamber.

Finally, it is not entirely excluded to use a small vacuum pump, for example of low capacity and reduced cost, in addition to the thermodynamic vacuum process, in cases where it is appropriate to accelerate timing or to obtain a high vacuum (e.g. in a final phase, in which there is no longer the risk that the pump can suck in condensed fluid).

The invention claimed is:

1. A sterilization method in a sterilization apparatus, the method comprising:
   performing at least an evacuation step of at least one sterilization chamber (1) in which a gaseous content of said at least one sterilization chamber (1) is made to pass through at least one condenser (3), and
   following said evacuation step, performing an evacuation cycle one or more times, the evacuation cycle comprising:
   isolating said at least one sterilization chamber (1) from said at least one condenser (3),
   operating at least one steam generator (2) to inject a predetermined amount of heated steam directly into said at least one condenser (3),
   cooling and condensing said steam in the at least one condenser (3) so as to reduce a volume of said steam and accordingly lower pressure within said at least one condenser (3) to below a pressure present in said at least one sterilization chamber, and
   placing said at least one condenser (3) in communication with said at least one sterilization chamber (1) to perform an evacuation.

2. The sterilization method as in claim 1, wherein a discharge valve (3c) is provided between said at least one condenser (3) and a drain tank (S1) to isolate said at least one condenser (3) from the drain tank (S1) during said cooling and condensing step.

3. The sterilization method as in claim 2, wherein said discharge valve (3c) isolates said at least one condenser (3) from the drain tank (S1) in a condition where a controlled inlet valve (2a) between said at least one steam generator (2) and the at least one sterilization chamber (1) is closed.

4. The sterilization method as in claim 1, wherein said at least one steam generator (2) is also connectable to said at least one sterilization chamber (1) and said cooling and condensing step is carried out by isolating said at least one steam generator (2) from the at least one sterilization chamber (1) and from the at least one condenser (3).

5. The sterilization method as in claim 1, wherein said step of operating at least one steam generator (2) to inject the predetermined amount of heated steam directly into said at least one condenser (3) results in expulsion of condensate present in the at least one condenser (3).

6. The sterilization method as in claim 1, wherein said evacuation cycle is performed in a final drying step.

7. The sterilization method as in claim 1, wherein said evacuation cycle is performed at an early stage to evacuate air and/or any fluids from the inside of said at least one sterilization chamber (1).

8. A sterilization system for performing a sterilization cycle, comprising:
   at least one airtight sterilization chamber (1), adapted to contain a load on which a sterilization cycle is performed,
   at least one steam generator (2) in fluid communication with said at least one airtight sterilization chamber (1) by means of a controlled inlet valve (2a),
   at least one condenser (3) in fluid communication with said at least one airtight sterilization chamber (1) by means of at least one controlled outlet valve (3a) connected to an inlet of the at least one condenser (3), the at least one condenser (3) apt to cool and condense steam received via the inlet from said at least one airtight sterilization chamber (1),
   wherein said at least one steam generator (2) is also connected to said at least one condenser (3) through the controlled inlet valve (2a) to generate and input steam, via the inlet of the at least one condenser (3), directly into said at least one condenser (3) in a condition where said at least one controlled outlet valve (3a) is closed so that the at least one airtight sterilization chamber (1) is isolated at least from said at least one steam generator (2).

9. The sterilization system as in claim 8, in which a discharge valve (3c) is arranged downstream of an outlet of said at least one condenser (3) with respect to the at least one steam generator (2) to discharge condensate and/or steam towards a collection tank (S1) via the outlet of said at least one condenser (3).

10. The sterilization system as in claim 9, wherein said discharge valve (3c) is provided between said at least one condenser (3) and said collection tank (S1) to isolate said at least one condenser (3) from the collection tank (S1).

11. The sterilization system as in claim 8, wherein said controlled inlet valve (2a) and said controlled outlet valve (3a) are independent and connected in fluid communication to each other (2c) and to the inlet of the at least one condenser (3).

12. The sterilization system as in claim 11, wherein said controlled inlet valve (2a) is operative as a controlled injection valve (2a) to the inlet of the at least one condenser (3).

* * * * *